(12) United States Patent
Telhan et al.

(10) Patent No.: US 12,378,511 B2
(45) Date of Patent: Aug. 5, 2025

(54) PORTABLE BIOREACTORS AND PORTABLE BIOREACTOR SYSTEMS FOR ANALYZING BIOFILM FORMATION AND DEGRADATION

(71) Applicants: The Trustees of the University of Pennsylvania, Philadelphia, PA (US); Biorealize, Inc., Philadelphia, PA (US)

(72) Inventors: Orkan Telhan, Philadelphia, PA (US); Karen Hogan, Philadelphia, PA (US)

(73) Assignees: The Trustees of the University of Pennsylvania, Philadelphia, PA (US); Biorealize, Inc., Philadelphia, PA (US)

( * ) Notice: Subject to any disclaimer, the term of this patent is extended or adjusted under 35 U.S.C. 154(b) by 498 days.

(21) Appl. No.: 17/284,415

(22) PCT Filed: Oct. 9, 2019

(86) PCT No.: PCT/US2019/055312
§ 371 (c)(1),
(2) Date: Apr. 9, 2021

(87) PCT Pub. No.: WO2020/076894
PCT Pub. Date: Apr. 16, 2020

(65) Prior Publication Data
US 2021/0340479 A1 Nov. 4, 2021

Related U.S. Application Data

(60) Provisional application No. 62/743,377, filed on Oct. 9, 2018.

(51) Int. Cl.
C12M 3/00 (2006.01)
C12M 1/00 (2006.01)
C12M 1/06 (2006.01)

(52) U.S. Cl.
CPC ............ *C12M 23/54* (2013.01); *C12M 23/28* (2013.01); *C12M 23/32* (2013.01); *C12M 27/02* (2013.01)

(58) Field of Classification Search
CPC ....... C12M 41/48; C12M 23/14; C12M 23/54
See application file for complete search history.

(56) References Cited

U.S. PATENT DOCUMENTS 8,697,430 B2    4/2014  Toguchida et al.
2005/0089993 A1*  4/2005  Boccazzi ................. C12M 1/12
                                                        435/297.5

(Continued)

FOREIGN PATENT DOCUMENTS

CN    102807953 A    12/2012
CN    106774516 A    5/2017

(Continued)

OTHER PUBLICATIONS

Extended European Search Report for European Patent No. 19871324.0 dated Sep. 9, 2022.

(Continued)

*Primary Examiner* — Jonathan M Hurst
(74) *Attorney, Agent, or Firm* — Morgan, Lewis & Bockius LLP

(57) ABSTRACT

The present disclosure is directed to portable bioreactors that allow the custom production of microbial cultures, and in some embodiments, the production of custom microbial biofilms. Also disclosed are portable bioreactor systems that are networked and capable of cooperative work in parallel.

7 Claims, 5 Drawing Sheets

(56) References Cited

U.S. PATENT DOCUMENTS

| | | | |
|---|---|---|---|
| 2010/0099172 A1* | 4/2010 | West | G05B 15/02 |
| | | | 435/286.1 |
| 2010/0330663 A1 | 12/2010 | Baumfalk | |
| 2011/0281343 A1* | 11/2011 | Gay | C12M 25/00 |
| | | | 435/287.1 |
| 2012/0156762 A1 | 6/2012 | Csányi et al. | |
| 2013/0177972 A1* | 7/2013 | Green | G06K 19/067 |
| | | | 235/487 |
| 2015/0218504 A1* | 8/2015 | Mangiacotti | C12M 1/36 |
| | | | 700/266 |
| 2017/0107477 A1* | 4/2017 | Farmer | C12N 1/20 |
| 2018/0051243 A1 | 2/2018 | Hogan et al. | |
| 2018/0273885 A1 | 9/2018 | Eisenkraetzer et al. | |
| 2019/0137338 A1* | 5/2019 | Webster | C12N 5/0636 |
| 2020/0165558 A1* | 5/2020 | Shevitz | C12M 27/04 |
| 2021/0108169 A1* | 4/2021 | Petersen | C12M 41/42 |

FOREIGN PATENT DOCUMENTS

| | | |
|---|---|---|
| EP | 2607474 A1 | 6/2013 |
| KR | 2012-0124277 A | 11/2012 |
| WO | 2010013419 A1 | 2/2010 |

OTHER PUBLICATIONS

International Search Report mailed Jan. 17, 2020 for International Patent Application No. PCT/US2019/055312.
Written Opinion mailed Jan. 17, 2020 for International Patent Application No. PCT/US2019/055312.
"How to Wind and Tie Yarn Skeins," Dummies a Wiley Brand, May 30, 2018 (May 30, 2018), pp. 1-7, Retrieved from the Internet: <https://www.dummies.com/crafts/knitting/how-to-wind-and-tie-yarn-skeins/> on Apr. 8, 2021 (Apr. 8, 2021) entire document.
Tuli et al., J. Food Sci. Technol. 52:4669-4678 (2015).
Zhao et al., Scientific Reports vol. 6, Article 18469 (2016).
Wang et al., Scientific Reports vol. 4, Article 5346 (2014).
Kennedy et al., Nature Methods, 7:973-975 (2010).
Strobel, Methods Mol. Biol., 581:247-261 (2009).
Ellert and Grebe, Nature Methods, 8:360 (2011).
Partial European Search Report for European Patent No. 19871324.0 dated Jun. 21, 2022.
English Machine Translation of CN102807953 A.
English Machine Translation of KR2012-0124277 A.

* cited by examiner

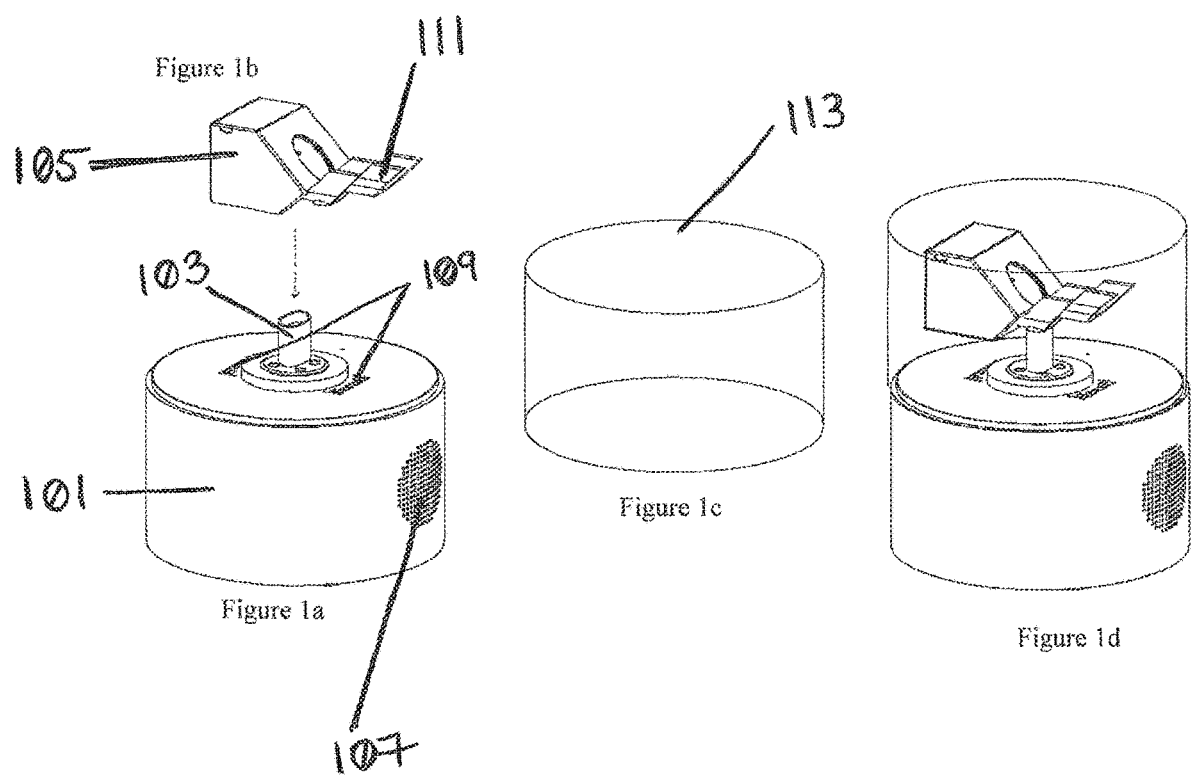

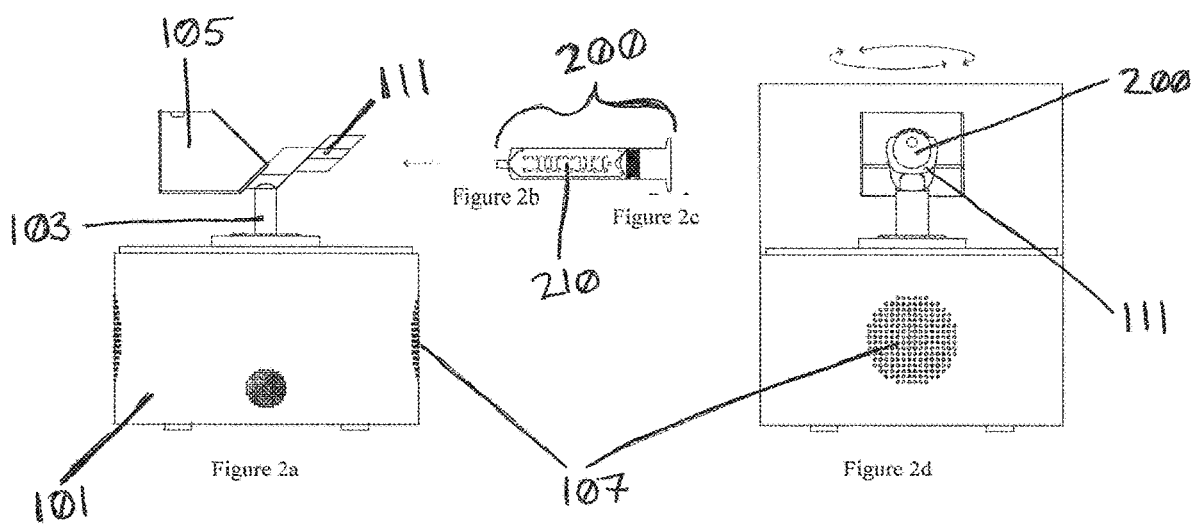

Figure 3a.
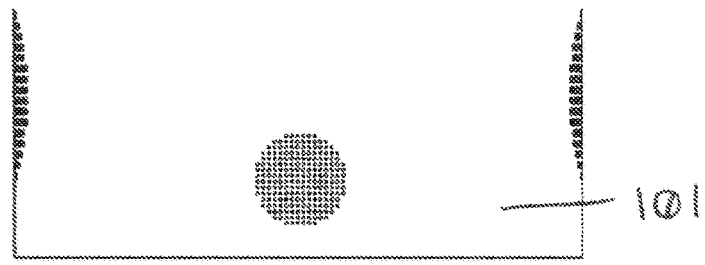
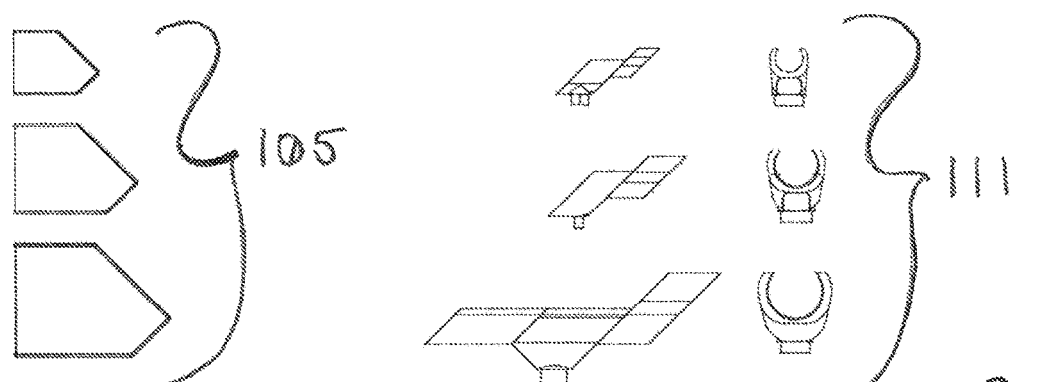
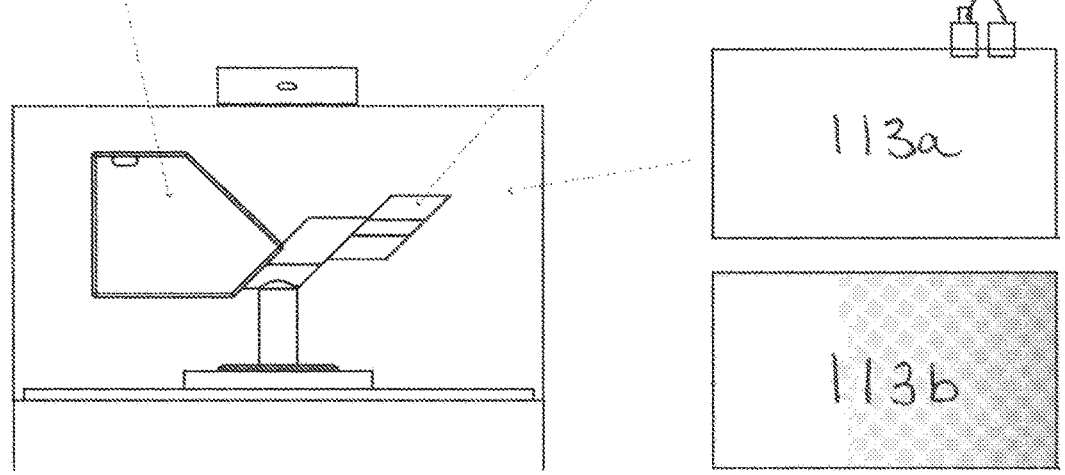
Figure 3b.

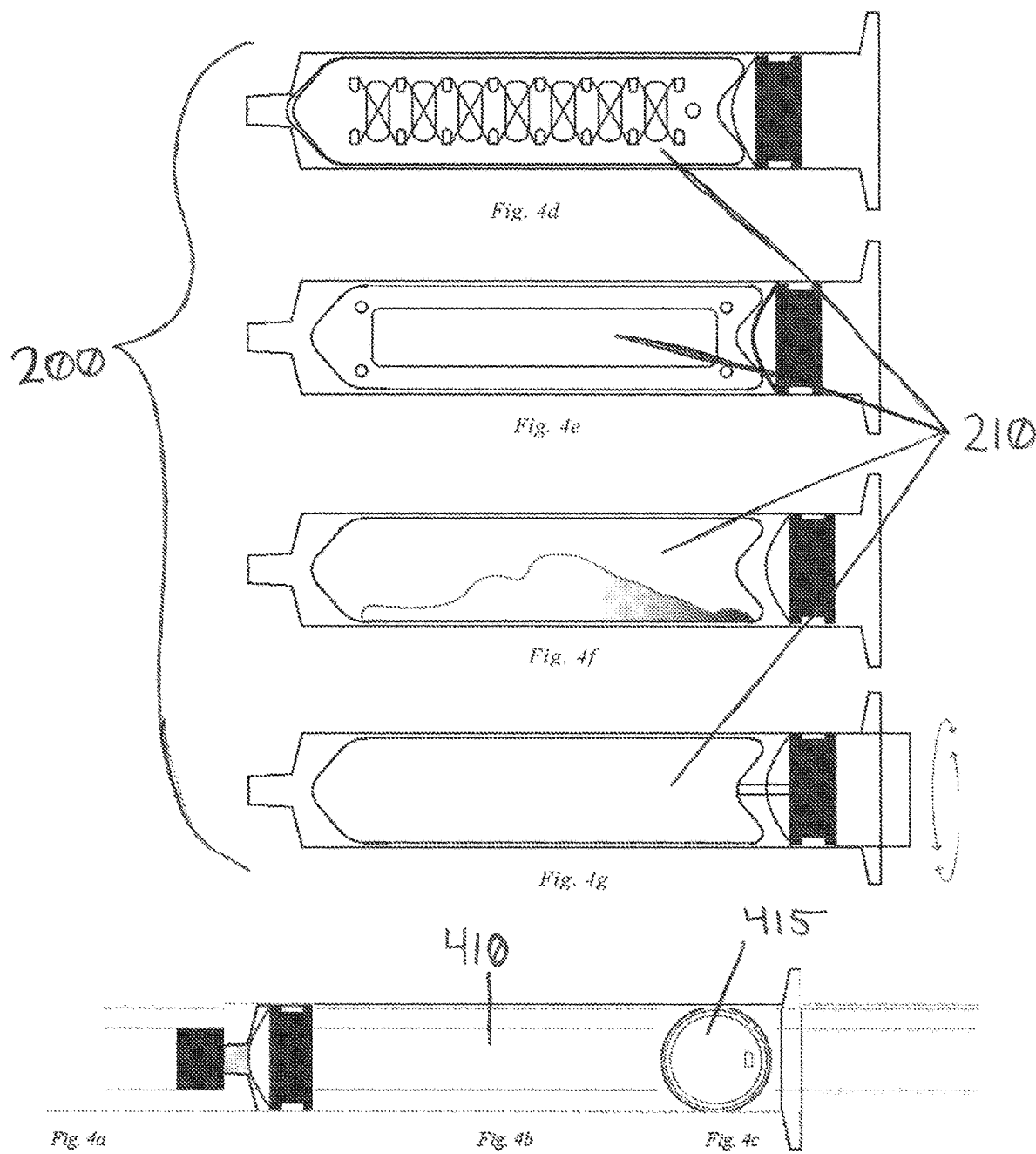

PORTABLE BIOREACTORS AND PORTABLE BIOREACTOR SYSTEMS FOR ANALYZING BIOFILM FORMATION AND DEGRADATION

CROSS REFERENCE TO RELATED APPLICATIONS

This application is a U.S. National Stage Patent Application of international PCT Patent Application No. PCT/US2019/055312, filed Oct. 9, 2019, which claims the benefit of U.S. Provisional Patent Application No. 62/743,377, filed Oct. 9, 2018, all of which is are hereby incorporated by reference in their entireties.

FIELD OF THE INVENTION

The invention described herein relates generally to portable bioreactor devices and more particularly, but not exclusively, to networked portable devices not reliant on an electric power grid, for growing microbes.

BACKGROUND

A significant technical problem in the field is the availability of a versatile, portable bioreactor systems, that can be used to culture a wide variety of cell lines, bacteria, fungi, yeast, and algae. In particular, networked portable bioreactors that are capable of off-electric grid operation. This present application discloses solutions to this technical problem.

SUMMARY

In some embodiments, the present invention provides for a portable bioreactor, the bioreactor comprising: (a) a base; (b) a lid capable of attaching to the top of the base forming a gas-tight seal; (c) a vessel holder for holding a culture vessel, with at one end a means for holding a culture vessel, and at the other end a means for operably connecting the vessel holder to the base to support the vessel holder for rotational movement; (d) a means for rotating the vessel holder about the vertical axis of the base.

In some embodiments, the present invention provides for a portable bioreactor system for growing microbes, the system comprising: memory; one or more processors; and one or more modules stored in memory and configured for execution by the one or more processors, the modules comprising instructions for: (a) agitating a culture vessel; (b) measuring a property of the culture vessel contents by operating a peripheral; and, (c) providing data to an external computer by means of a network connection.

BRIEF DESCRIPTION OF THE DRAWINGS

The foregoing summary, as well as the following detailed description of the invention, will be better understood when read in conjunction with the appended drawings.

FIG. 1 Depicts the principal components of the portable bioreactor. FIG. 1a depicts the base 101, the shaft 103 for rotating and/or vibrating the peripheral 105, which is shown in FIG. 1b. On the right surface of the base 101, the circular crosshatched area depicts an exemplary ambient air intake 107. The rectangular crosshatched areas at the base 101 of the shaft 103 are the air exhaust vents 109 for a temperature control system embodied in the base 101 of a bioreactor. FIG. 1b shows an exemplary peripheral 105 comprising a vessel holder 111 and a spectrometer. The peripheral 105 is operably attached to the shaft 103, depicted in FIG. 1a, allowing the peripheral 105 to be rotated or vibrated, or both rotated and vibrated. The shaft 103 also supports the peripheral 105 and may provide electrical power from the base 101 to the peripheral 105. The shaft 103 may also provide wired data connections, wired control connections, or both, between the base 101 and the peripheral 105. FIG. 1c, depicts an exemplary optically clear lid 113. FIG. 1d depicts the mating between the lid 113 of FIG. 1c and the base 101, FIG. 1a, forming a hermetically sealed chamber surrounding the peripheral 105.

FIG. 2 Depicts another view of an exemplary embodiment of a portable bioreactor. On the left and right side respectively, FIG. 2a shows crosshatched areas representing an air intake 107 for the heating and cooling system respectively. FIG. 2b depicts an exemplary vessel 200 with a plug. Inside the syringe embodiment of a vessel 200 is an exemplary mount 210, shown in FIG. 2c. Such a mount 210 may be used to hold yarn, exposing the yarn or other corded material to the contents of the vessel 200. The exemplary mount 210 has a two by eight array of posts orthogonal to the plane of the long dimension of the mount 210. These posts, or pegs, are suitable for arranging the corded material in a zig-zag, crisscrossing pattern, increasing the exposed surface area of the corded material to the contents of the vessel 200. FIG. 2d shows a side view with an exemplary air intake 107, which could be either for a heating or cooling system (stippled circular area). This side view depicts a syringe embodiment of a vessel 200 resting in a vessel holder 111 with a semi-circular profile to hold the cylindrical vessel 200. In the background the peripheral 105 portion of the vessel holder 111 is visible. The arrows above the optically clear lid 113 illustrate the capability of the shaft 103 to rotate the vessel holder 111 and peripheral 105 assembly either clockwise or counterclockwise.

FIG. 3 Depicts the relationship between an exemplary vessel holder 111 comprising modular cradles capable of holding different size vessels 200 and modular peripherals 105. Each peripheral 105 comprises a means for executing a function, for example, measuring pH, gas tension, optical density, performing polymerase chain reactions (PCR), performing spectroscopic measurements, for example, UV-VIS, NIR, or IR spectroscopy, without interrupting the culturing process. In some embodiments, such functions are executed inline without interrupting the culturing process. FIG. 3b depicts two light-filtering exemplary embodiments of lids 113. The top example comprises gas out-flow and gas in-flow ports. The middle example comprises light filtering lid 113 and the lower embodiment comprises a visible light opaque lid 113.

FIG. 4 Depicts various mount 210 embodiments each of which are inserted inside a syringe vessel 200. FIG. 4a shows a peripheral 105 module comprising a means for performing genetic modification of an organism, such as, but not limited to, using electroporation. FIG. 4b shows a variable position plug 410 attached to a plunger. Depicted in FIG. 4c is a near field communication (NFC) tag 415, which encodes information related to the contents of the vessel 200 and parameters or information related to the contents of the vessel 200. FIG. 4d shows a yarn or corded material mount 210 support. The mount 210 has a series of seven fenestrations to facilitate the flow of the contents of vessel 200 over corded material. Corded material may be arranged in various patterns using the two by eight array of posts, for example, a crisscross pattern as shown in FIG. 4d. FIG. 4e shows an exemplary embodiment of a cassette holding a two dimensional film is inserted inside the vessel 200. A cassette holds the film, exposing the film to the contents of the vessel 200. Such a film may be a surface upon which microbes are cultured, to produce an engineered biofilm. FIG. 4f shows a non-limiting example of a three dimensional soft material inside a syringe embodiment of the vessel 200. The soft material is exposed to the contents of the vessel 200 and the soft material may be a surface upon which microbes are cultured to produce a biofilm.

FIG. 5 Depicts exemplary portable bioreactor system 500 embodiments.

DETAILED DESCRIPTION OF THE INVENTION

Figure 5A:
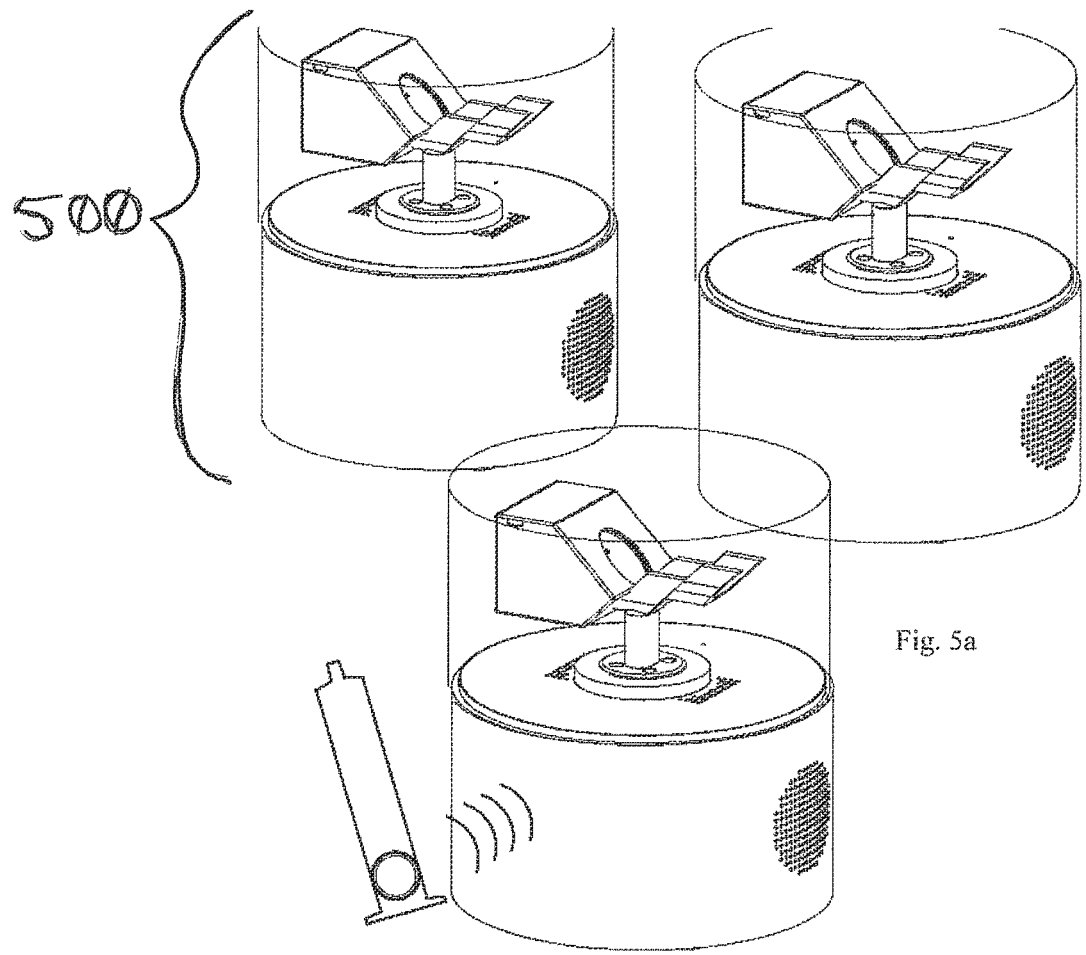
FIG. 5a shows a flexible near field communication (NFC) device attached to a vessel 200 and communicating information wirelessly to the portable bioreactor system 500.

Unless defined otherwise, all technical and scientific terms used herein have the same meaning as is commonly understood by one of skill in the art to which this invention belongs. All patents and publications referred to herein are incorporated by reference in their entireties.

Microbes are a rich source of pigmented organic molecules. Pigment producing microorganisms are known to the art and recognized as being a rich source of natural colors. Tuli et al., *J. Food Sci. Technol.* 52:4669-4678 (2015) compile a list of exemplar microorganisms capable of producing pigments spanning the spectrum from red to violet. However, despite the wide variety of microorganisms that produce pigmented molecules, there are substantial challenges to culturing many of these organisms, even on small scale.

A use for portable bioreactors are to culture microorganisms under conditions to produce microbial pigments. Pigments may be extracted from microorganisms and then textiles or other materials dyed with the microbial pigments. For example, yarn may be dyed with a portable bioreactor, it shakes, heats and feeds the organisms at different media and culturing settings. We also work with organisms to remediate existing yarn to change their color and make them less toxic. Many types of yarn in different materials, thickness, and strength, can be dyed using customized mounts 210. First we program the bioreactor for temperature and agitation speed. Then, we grow the organisms in special media to make the pigments. When there are enough pigments are grown, we insert the dyeing mount 210 and submerge the yarn in it. Depending on the type of pigment, the yarn gets ready within 12 to 24 hours. Then we can wash, sterilize, and treat the yarn for the application.

Uses for various embodiments of portable bioreactors include, but, are not limited to fermentation, anaerobic microbial culturing, aerobic microbial culturing, animal cell culturing, tissue culturing, one dimensional, two dimensional, or three dimensional biofilm growth, biofilm manufacturing, biofilm modification, biofilm analysis, biofilm degradation, nucleic acid detection, nucleic acid amplification (e.g. quantitative polymerase chain reaction (qPCR), reverse transcription polymerase chain reaction (rtPCR), small molecule detection, and diagnostic tests.

Definitions

"Peripheral" is defined as a module or unit that may be optionally attached to the vessel holder. Such a peripheral may add functionality to the bioreactor, for example, and without limitation, add a means for measuring temperature or add a means for measuring optical density of the contents of the vessel.

"Mount" is defined as a module that is placed inside a vessel providing support for materials to be exposed to the contents of the vessel. "Mount" also includes the term material attachment mechanism.

For the avoidance of doubt, it is intended herein that particular features (for example integers, characteristics, values, uses, diseases, formulae, compounds or groups) described in conjunction with a particular aspect, embodiment or example of the invention are to be understood as applicable to any other aspect, embodiment or example described herein unless incompatible therewith. Thus such features may be used where appropriate in conjunction with any of the definition, claims or embodiments defined herein. All of the features disclosed in this specification (including any accompanying claims, abstract and drawings), and/or all of the steps of any method or process so disclosed, may be combined in any combination, except combinations where at least some of the features and/or steps are mutually exclusive. The invention is not restricted to any details of any disclosed embodiments. The invention extends to any novel one, or novel combination, of the features disclosed in this specification (including any accompanying claims, abstract and drawings), or to any novel one, or any novel combination, of the steps of any method or process so disclosed.

Portable Bioreactors

In some embodiments, the present disclosure provides for a portable bioreactor, the bioreactor comprising: (a) a base 101; (b) a lid 113 capable of attaching to the top of the base 101 forming a gas-tight seal; (c) a vessel holder 111, at one end a means for holding a vessel 200, and at the other end a means for operably connecting the vessel holder 111 to the base 101 to support the vessel holder 111 for rotational movement; (d) a culture vessel 200; and, (e) a means for rotating the vessel holder 111 about the vertical axis of the base 101.

In some embodiments, the present disclosure provides for a portable bioreactor, the bioreactor comprising: (a) a base 101; (b) an axial shaft 103 operably connected to a means for rotating the shaft 103, the axial shaft 103 projecting out of the top of the base 101; (c) a lid 113 capable of attaching to the top of the base 101 forming a gas-tight seal; (d) a vessel holder 111, at one end a means for holding a vessel 200, and at the other end a means for operably connecting the vessel holder 111 to the axial shaft 103 to support the vessel holder 111 and for rotational movement; and, (e) a culture vessel 200.

In some embodiments the vessel holder 111 is a peripheral 105. In some embodiments, the means for operably connecting the vessel holder 111 to the base 101 is an axial shaft 103 capable of rotating the vessel holder 111. FIG. 1a shows a non-limiting exemplary base 101 comprising an axial shaft 103 operably connecting a vessel holder 111 to the base 101, wherein the base 101 further comprises a means for rotating the axial shaft 103 and the operably connected vessel holder 111.

In some embodiments, the vessel holder 111 further comprises a means to heat and cool the vessel 200. In some embodiments, the vessel holder 111 comprises a thermoelectric cooling module.

In some embodiments, the vessel holder 111 comprises modular cradles holding vessels 200 of varying sizes. FIG. 3a show non-limiting examples of modular cradles.

In some embodiments, the vessel holder 111 comprises (a) a vessel holder 111; (b) a peripheral 105; and (c) a means to operably connect the bottom of the vessel holder 111 to the axial shaft 103.

In some embodiments, the base 101 further comprises a battery module enabling the portable bioreactor to operate without access to electric power grid power. In some embodiments, the base 101 further comprises a solar charging system to recharge the battery module. In some embodiments, the peripheral 105 controls the battery module. In some embodiments, the peripheral 105 controls the solar charging system.

In some embodiments, the present disclosure provides for a portable bioreactor, the bioreactor comprising: (a) a base 101; (b) a lid 113 capable of attaching to the top of the base 101 forming a gas-tight seal; (c) a vessel holder 111, at one end a means for holding a vessel 200, and at the other end a means for operably connecting the vessel holder 111 to the base 101 to support the vessel holder 111 for rotational movement; (d) a culture vessel 200; (e) at least one peripheral 105, wherein the peripheral 105 is attached to the vessel holder 111; and, (f) a shaft 103 for rotating the vessel holder 111 about the vertical axis of the base 101.

Peripherals

In some embodiments, the bioreactor further comprises one or more peripheral 105s. A peripheral 105 may perform one or more function. A peripheral 105 is controlled by the portable bioreactor system 500. FIG. 1b shows a non-limiting exemplary peripheral 105.

Peripherals 105 are modular units that attach to the vessel holder 111, the vessel holder 111 providing electrical connections to the peripheral 105. In some embodiments, the vessel holder 111 further comprises a data connection between the base 101 and peripheral 105. In some embodiments, the data and power connections for a peripheral 105 is provided via the shaft 103 connection.

In some embodiments, a peripheral 105 provides a means to electroporate microbes. FIG. 4a depicts a non-limiting example of an electroporation peripheral 105 attached to an exemplary vessel 200. Small, flow-through electroporation devices are known to the skilled artisan, for example, Zhao et al., describe typical devices, in *Scientific Reports* volume 6, Article number: 18469 (2016). Zhao et al., FIG. 1, depicts an exemplary means for performing electroporation.

In some embodiments, the peripheral 105 measures the pH of the contents of the culture vessel 200. In some embodiments, the peripheral 105 measures the ambient temperature inside the gas-tight sealed chamber. In some embodiments, the peripheral 105 measures the temperature of the contents of the culture vessel 200. In some embodiments, the peripheral 105 measures the optical density of the contents of the culture vessel 200. In some embodiments, the peripheral 105 measures the optical density of the contents of the vessel 200 at at least one wavelength in the range from about 340 nm to about 850 nm. In some embodiments, the peripheral 105 measures the optical density of the contents of the culture vessel 200 at at least one wavelength in the range between 600 nm and 800 nm. In some embodiments, the peripheral 105 measures the optical density of the contents of the culture vessel 200 at 600 nm. In some embodiments, the peripheral 105 measures the optical density by scanning the wavelength range between about 600 nm to about 800 nm. In some embodiments, the data measured by the peripheral 105 is transmitted to the base 101 via the shaft 103 through a wired connection or transmitted to an external computer by means of a wireless connection.

In some embodiments, the peripheral 105 comprises a means for withdrawing a portion of the contents of the culture vessel 200. In some embodiments, the peripheral 105 comprises a means for performing a polymerase chain reaction on the portion removed from the culture vessel 200. In some embodiments, the peripheral 105 comprises a means for performing multiwavelength spectroscopy on the portion removed from the culture vessel 200. In some embodiments, the means for performing multiwavelength spectroscopy performs UV-VIS, NIR, or IR spectroscopy. In some embodiments, the means for performing multiwavelength spectroscopy performs UV-VIS, NIR, or IR spectroscopy without interrupting the culturing process. In some embodiments, the means for performing multiwavelength spectroscopy performs UV-VIS, NIR, or IR spectroscopy, performs the spectroscopy inline without interrupting the culturing process.

In some embodiments, the peripheral 105 comprises a means to heat and cool the vessel 200. In some embodiments, the peripheral 105 comprises a thermoelectric cooling module.

In some embodiments, the culture vessel holder 111 can be used to perform polymerase chain reaction (PCR) inside the culture vessel 200 by heating and cooling the holder 111. In some embodiments, the holder 111 is made from a thermally conductive material (for non-limiting example, aluminum alloys), which can heat and cool the vessel 200 employing a thermoelectric module.

In some embodiments, the peripheral 105 comprises a means for heating, cooling, or both heating and cooling the contents of the culture vessel 200. In some embodiments, the peripheral 105 comprises a heating and a cooling unit.

In preferred embodiments, a peripheral 105 provides a means to perform an analytical function on the contents of the culture vessel 200. In some embodiments, the analytical function comprises measuring one or more of the following non-limiting parameters: temperature, gas tension, $pCO_2$, $pO_2$, percent oxygen, percent nitrogen, pH, and ionic strength.

In some embodiments, a peripheral 105 comprises a motor apparatus that can rotate the material attachment mechanisms for controlling the amount of immersion of the biofilm in liquid or solid media, see an exemplary arrangement of components in FIG. 4g.

In some embodiments, the material attachment mechanism, also termed mount 210, can be made from liquid-dissolvable material that is adapted so as to degrade over time. The motor apparatus can automatically move the plunger in the horizontal axis to dispense the remains of the material attachment, the cultured organisms, the biofilms or media outside of the vessel 200 through its tip.

In some embodiments, the vessel holder 111 further comprises a motor apparatus that can rotate a mount 210 enclosed within the culture vessel 200. In some embodiments, the vessel holder 111 further comprises a motor apparatus that can rotate the material attachment mounts 210 for controlling the amount of immersion of the biofilm in liquid or solid media, see an exemplary arrangement of component in FIG. 4g.

Lids

In some embodiments, the lid 113 forms a gas-tight seal with the base 101. In some embodiments, the lid 113 further comprises a means to vent the interior volume to the outside ambient atmosphere. In some embodiments, the lid 113 further comprises a means to introduce gas into the interior volume. In some embodiments, the means to introduce gas into the interior volume is through electro-mechanical valves. In some embodiments, the means to introduce gas into the interior volume is through diaphragms. In some embodiments, the valve can be controlled through a solenoid, which can modulate the opening and closing of the inlet and outlet. In some embodiments, the opening and closing can be controlled through a piezoelectric diaphragm.

In some embodiments, the lid 113 further comprises means for measuring one or more of atmospheric pressure, temperature, humidity, gas composition, and photon flux.

In some embodiments, the lid 113a is optically clear. In some embodiments, the lid 113b is optically opaque. In some embodiments, the lid 113 is an optical band pass filter which can pass through or filter light in specific wavelengths.

In some embodiments, the lid 113 further comprises an ultraviolent (UV) lamp. Such a lamp may be used to kill the cultured microorganisms for sterilization purposes. In some embodiments, the UV lamp is used after the culture is complete terminate microbial growth. The lamp is activated for a sufficient period of time to sanitize the vessel 200 content and the chamber. In some embodiments, the UV lamp is used to sterilize the interior of the bioreactor. In some embodiments, the UV lamp is used to sterilize the base 101, the contents of the culture vessel 200, the vessel holder 111, and the one or more attached peripherals 105.

In some embodiments, the lid 113 further comprises a visual light opaque material. In some embodiments, the opaque lid 113 further comprises light source, wherein the light source can produce a specific wavelength of light. Such a tunable wavelength light source can enable culturing organisms particularly stimulated by a wavelength or for conducting optogenetic experiments, in which the light source can be fixed, moveable and controlled by the portable bioreactor system 500.

In some embodiments, the light source can be adjusted to a wavelength to activate light sensitive genetic modules in microorganisms. Such light sensitive genetic modules may be engineered to regulate the expression of genes related to pigment biosynthesis or biofilm production. For example, Wang et al., *Scientific Reports* volume 4, Article number: 5346 (2014), describe optically controllable gene expression models and methods. Kennedy et al., *Nat. Meth.,* 7, 973-975 (2010), describe other methods to monitor protein::protein interactions via blue light.

In some embodiments, the bioreactor lid 113 can have a dispense mechanism that can load or unload media, organisms, or assays onto the culturing vessels 200 below. In some embodiments the dispense mechanism can transfer liquid or solid payload by rotating the culturing vessels 200 under specific inlets/outlets on which payload can be deposited. In some embodiments, the transfer can be performed by a 2- or 3-axis translational movement mechanism that can pick and place or drop payloads onto the culturing vessel 200 that remains stationary.

Vessels

In some embodiments the vessel 200 comprises a syringe. In some embodiments the syringe comprises a commercially available, disposable syringe. In some embodiments the syringe comprises a commercially available, reusable-glass syringe. In some embodiments the syringe includes miniaturized analytical instrumentation embedded in the plunger that is capable of monitoring contents of the syringe. FIG. 2b shows a non-limiting exemplary embodiment of a vessel 200 comprising a syringe. In an embodiment, vessel holder 111 is complimentary shaped hold a vessel 200. In an embodiment, the vessel holder 111 comprises a means for retaining the vessel 200 while the vessel holder 111 rotates. In some embodiments the means for retaining the vessel 200 is a frictional fit between the vessel 200 and the vessel holder 111. In some embodiments, the means for retaining the vessel 200 comprises retention latches.

In some embodiments the vessel 200 further comprises one or more ports that pass through the plunger and permit monitoring of gas tension in contents of the syringe. In some embodiments, the one or more ports that pass through the plunger permit control of gas tension in the contents of the syringe.

In some embodiments, the vessel 200 may further comprise a custom tip. Such a tip has the physical dimensions and sealing functions of a syringe plug 410. In some embodiments, the tip can include two electrodes, which can be connected to the peripheral 105 for transmitting high voltage electricity to the vessel 200 to do electroporation. In some embodiments, the tip may include probes, which can be used by a peripheral 105 to measure cellular density of a fluid contained in the vessel 200 using capacitive measurement.

In some embodiments vessel 200 holds a minimum of about 1 mL, 2 mL, 5 mL, 10 mL, or about 20 mL of liquid. In some embodiments the vessel 200 holds a maximum of about 100 mL, about 50 mL, about 20 mL, about 10 mL, about 5 mL, or about 1 mL (min) of liquid. However, it is foreseen that the different embodiments of the platform can utilize different vessel 200 sizes for different applications.

In some embodiments, a mount 210 is inserted inside the vessel 200. FIG. 4d shows a non-limiting example of a mount 210 inside a syringe embodiment of the vessel 200. In some embodiments, the mount 210 holds an essentially one dimensional material. For example, a one dimensional material held by a mount 210 may be yarn or other cord material, exposing the yarn or cord material to the contents of the vessel 200. In some embodiments, the essentially one dimensional material is the surface upon which microbes are cultured.

In preferred embodiments, the mount 210 comprises a surface for biofilm growth. In some embodiments, the mount 210 comprises a polymer surface for biofilm growth. In some embodiments, the mount 210 comprises a glass surface for biofilm growth. In some embodiments, the mount 210 comprises cassette holding a film. is inserted inside the vessel 200. FIG. 4e shows a non-limiting example of a cassette holding a film inside a syringe embodiment of the vessel 200. A cassette holds the film, exposing the film to the contents of the vessel 200. In some embodiments, the film is the surface upon which microbes are cultured.

In some embodiments, a soft material is inserted inside the vessel 200. FIG. 4f shows a non-limiting example of a soft material inside a syringe embodiment of the vessel 200. The soft material is exposed to the contents of the vessel 200. In some embodiments, the soft material is the surface upon which microbes are cultured. In some embodiments, the soft material is a hydrogel upon which microbes are cultured. In some embodiments, the soft material is a gelatinous material. In some embodiments, the soft material is Polydimethylsiloxane (PDMS) based material.

Bases

In some embodiments, the means for rotating the vessel holder 111 about the vertical axis of the base 101 is a motor operably connected by a shaft 103 to the vessel holder 111. In some embodiments, the operably connected motor may rotate the vessel holder 111. In some embodiments, the operably connected motor may vibrate the vessel holder 111. The rotation and vibration are sufficient to allow gas exchange between a liquid in the vessel 200 and the covering gas in the vessel 200. In some embodiments, the rotation is continuous at a fixed rate; in some embodiments, the rotation is periodic. In some embodiments, rotation and vibration are alternated. In some embodiments, the base 101 further comprises a means for measuring the absolute angular position of the vessel holder 111. In some embodiments, the base 101 is adapted for controlling the rotation of the vessel holder 111, while monitoring the angular position and rotational speed of the vessel holder 111. In some embodiments, the base 101 is further adapted to communicate vessel holder 111 position and speed to a peripheral 105. In some embodiments, the base 101 is further adapted to communicate vessel holder 111 position and speed to an external computer.

In some embodiments, the operably connected motor may spin the vessel holder 111 at a sufficient number of revolutions per minute to generate sufficient relative centrifugal force to collect microbial cells suspended in a liquid inside the vessel 200. In some embodiments the relative centrifugal force is in the range between about 500 and about 5000 RCF.

In some embodiments, the base 101 provides a means for evacuating the interior volume enclosed by the lid 113. In some embodiments the means for evacuating the enclosed volume is a compact pump. In some embodiments the means for evacuating the interior volume is a system that opens an out-flow valve and in-flow valve, allowing an essentially oxygen-free gas to purge the interior volume, replacing the volume with the essentially oxygen-free gas. Such means enable microbial culturing in low-oxygen or anaerobic conditions. For example, Strobel, *Methods Mol. Biol.*, 581:247-261 (2009), describes basic methods for culturing anaerobic bacteria. Bioreactor embodiments disclosed herein are suitable for such anaerobic culture methods.

In some embodiments, referring to FIG. 1*a*, FIG. 1*d*, and FIG. 2*a*, the base 101 further comprises a means for heating and cooling the vessel 200. In some embodiments the means for heating and cooling the vessel 200 comprises one or more fans and a plurality of thermoelectric elements. In an embodiment, the one or more fans intake air from the ambient atmosphere and blow it into the interior volume of the enclosed chamber. Together with a temperature sensor, the heating-cooling system creates a climate controlled environment for cell incubation and biofilm formation. In some embodiments, the bioreactor interior volume temperature, is controlled via a feedback controller. In some embodiments, the temperature is modulated by a portable bioreactor system 500 as disclosed herein. In some embodiments, the temperature may vary according to a programmed schedule.

Sample Tracking

In some embodiments, the portable bioreactor further comprises a module that reads data from a wireless identification tag 415 such as a flexible near field communication (NFC) tag 415 attached to a vessel 200. In some embodiments, the bioreactor can be controlled through the wireless identifiers mounted onto the vessel 200*s*, in which the vessel 200 becomes both the activator of the device and contains parameters for the experiment. In such embodiments, the bioreactor system 500 further comprises NFC reader module and NFC writer module that is capable of encoding and decoding information stored on the NFC vessel 200 identifiers.

In some embodiments the culturing vessel 200*s* are identified with wireless identification tags for example, NFC tags 415, wherein such tags are adapted to store one or more of the following: information about the contents of the vessel 200 to which it is attached, administrative information related to the sample, a bioreactor assignment, an assigned culturing protocol for the sample, information about the experiment, data storage information, encryption information, and data transmission information. See, for example, FIG. 4*c* and FIG. 5*a*. This NFC tracking allows the vessel 200 to be keyed to a specific user, for non-limiting example, for safety, chain-of-custody, or security purposes. and limits data breach. In some embodiments, the portable bioreactor can be connected to the internet and reading the NFC tag 415 data of a vessel 200, the portable bioreactor can download a culture protocol from a remote database, then implement the culture protocol.

Portable Bioreactor Systems

In some embodiments, the present disclosure provides for a portable bioreactor system for growing microbes, the system 500 comprising: memory; one or more processors; and one or more modules stored in memory and configured for execution by the one or more processors, the modules comprising instructions for: (a) agitating a culture vessel 200; (b) measuring a property of the culture vessel 200 contents by operating a peripheral 105; and, (c) providing data to an external computer by means of network connection.

In some embodiments, the portable bioreactor system 500 further comprises a data storage module which is operably connected to the memory and one or more processors. In some embodiments, the data storage module is a solid state storage module allowing reading and writing of data from and to the module. Exemplary embodiments are suitable for remote data logging applications or remote operation of the portable bioreactor system 500.

Peripherals

In some embodiments, the portable bioreactor system 500 further comprises one or more peripherals 105. A peripheral 105 may perform one or more function. A peripheral 105 is controlled by the portable bioreactor system 500. FIG. 1*b* shows a non-limiting exemplary peripheral 105.

Peripherals 105 are modular units that attach to the vessel holder 111, the vessel holder 111 providing electrical connections to the peripheral 105. In some embodiments, the vessel holder 111 further comprises a data connection between the base 101 and peripheral 105. In some embodiments, the data and power connections for a peripheral 105 is provided via the shaft 103 connection.

In some embodiments, the peripheral 105 is adapted for data processing independent from the portable bioreactor system 500. In some embodiments, the peripheral 105 independently comprises: memory, one or more processors, a data storage module which is operably connected to the memory and one or more processors. In some embodiments, the peripheral 105 further comprises a network interface adapted for communication to the portable bioreactor system 500. In some embodiments, the peripheral 105 further comprises a network interface adapted for communication to a computer.

In some embodiments, a peripheral 105 provides a means to electroporate microbes. FIG. 4*a* depicts a non-limiting example of an electroporation peripheral 105 attached to an exemplary vessel 200. Small, flow-through electroporation devices are known to the skilled artisan, for example, Zhao et al., describe typical devices, in *Scientific Reports* volume 6, Article number: 18469 (2016). Zhao et al., FIG. 1, depicts an exemplary means for performing electroporation.

In some embodiments, the peripheral 105 measures the pH of the contents of the culture vessel 200. In some embodiments, the peripheral 105 measures the ambient temperature inside the gas-tight sealed chamber. In some embodiments, the peripheral 105 measures the temperature of the contents of the culture vessel 200. In some embodiments, the peripheral 105 measures the optical density of the contents of the culture vessel 200. In some embodiments, the peripheral 105 measures the optical density of the contents of the vessel 200 at at least one wavelength in the range from about 340 nm to about 850 nm. In some embodiments, the peripheral 105 measures the optical density of the contents of the culture vessel 200 at at least one wavelength in the range between 600 nm and 800 nm. In some embodiments, the peripheral 105 measures the optical density of the contents of the culture vessel 200 at 600 nm. In some embodiments, the peripheral 105 measures the optical density by scanning the wavelength range between about 600 nm to about 800 nm. In some embodiments, the data measured by the peripheral 105 is transmitted to the base 101 via the shaft 103 through a wired connection or transmitted to an external computer by means of a wireless connection.

In some embodiments, the peripheral 105 comprises a means for withdrawing a portion of the contents of the culture vessel 200. In some embodiments, the peripheral 105 comprises a means for performing a polymerase chain reaction on the portion removed from the culture vessel 200. In some embodiments, the peripheral 105 comprises a means for performing multiwavelength spectroscopy on the portion removed from the culture vessel 200. In some embodiments, the means for performing multiwavelength spectroscopy performs UV-VIS, IR, or NIR spectroscopy.

In some embodiments, the peripheral 105 comprises a means to heat and cool the vessel 200. In some embodiments, the peripheral 105 comprises a thermoelectric cooling module.

Networking

In some embodiments, the bioreactor system 500 further comprises a network communication module operably connected to the one or more processors. In some embodiments, multiple bioreactor systems 500 can be connected to each other via the network communication module enabling the multiple bioreactors to execute experiments in parallel. In some embodiments, the networked multiple bioreactor systems 500 cooperatively execute individual experiments that together constitute a designer of experiment (DOE) to identify the relationships between factors affecting the outcome of the culturing process. Ellert and Grebe discuss such approaches in *Nature Methods*, 8:360 (2011). FIG. 3, therein, depicts a typical analysis of a two-factor experiment.

Figure 5B:
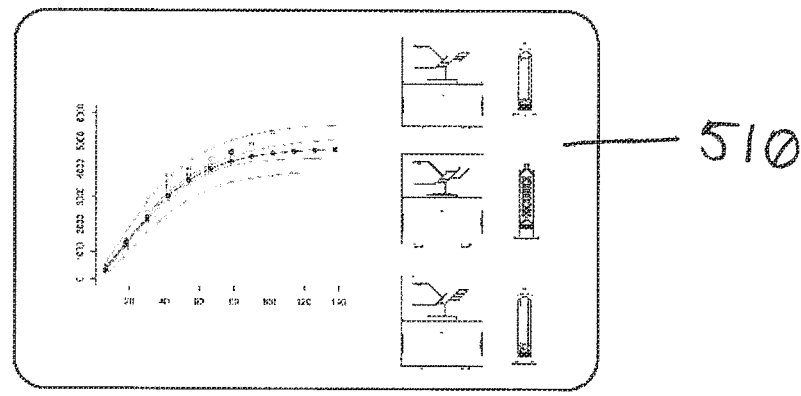
FIG. 5b depicts an exemplary user interface 510 wherein an exemplary portable bioreactor system 500 wirelessly communicates information related to the microbial culture to an external computer. This figure illustrates that more than one portable bioreactor unit may operate in parallel or operate cooperatively through network connections.

In some embodiments, the data communicated to the remote computer is used to monitor the health, culture growth status, and other parameters associated with each bioreactor system 500. The plurality of the data communicated from the plurality of bioreactor systems 500 can be used to do comparative analysis that is distributed across machines located together or in various remote location. FIG. 5b shows an exemplary embodiment of three portable bioreactor systems 500 wirelessly networked.

In some embodiments, a portable bioreactor system 500 is connected to a web-based user interface 510 that can be displayed, for example, on a smart phone or tablet. In some embodiments, the web-based user interface 510 enables real-time analysis of the operation of the bioreactor system 500, and in particular, to monitor the progress of microbial growth. In some embodiments, the web-based user interface 510 allows monitoring video and still images captured by a peripheral 105 with a camera or other means for capturing image data. In embodiments, the web-based user interface 510 receives data related to the system health, operating status, or operating parameters of a portable bioreactor system 500.

Voice Control

In some embodiments, the portable bioreactor system 500 further comprises a voice control module allowing spoken commands to control the system. In some embodiments, the bioreactor system 500 further comprises an audio output module (e.g. a speaker) for reporting status, experimental data, and system health, information. Together with the voice control module and audio output module, these features augment and substitute the need for continuous visual monitoring.

In some embodiments, the portable bioreactor system 500 is equipped with a microphone enabling it to be controlled through a voice-recognition interface module. In some embodiments, the portable bioreactor system 500 bioreactor is equipped with a speaker to provide audio feedback to the user, the system reporting process progress, results, and termination, such as indicating when experiment is done or when a target outcome is achieved. Together with the microphone and speaker, these features augment and substitute the need for continuous visual monitoring, as non-limitingly exemplified by FIG. 2a.

Sample Tracking

In some embodiments, the portable bioreactor system 500 reads data from a flexible wireless identification tag, such as a flexible near field communication tag 415 attached to a vessel 200. In some embodiments, the portable bioreactor system 500 can be controlled through the wireless identifiers mounted on the culture vessel 200s, wherein the vessel 200 becomes both activates the bioreactor and contains parameters for the experiment executed by the bioreactor. In such embodiments, the bioreactor system 500 further comprises a wireless communication module adapted to read and write data to an external device, for example, and without limitation, a near field communication (NFC) module, wherein the NFC reader module and NFC writer module that is capable of encoding and decoding information stored on the NFC vessel 200 identifiers.

While preferred embodiments of the invention are shown and described herein, such embodiments are provided by way of example only and are not intended to otherwise limit the scope of the invention. Various alternatives to the described embodiments of the invention may be employed in practicing the invention.

EXAMPLES

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

Example 1

A use for portable bioreactors are to culture microorganisms under conditions to produce microbial pigments. Pigments may be extracted from microorganisms and then textiles or other materials dyed with the microbial pigments. For example, yarn may be dyed with a portable bioreactor, which shakes, heats, and feeds the organisms using different media and culturing settings. We also work with organisms to remediate existing yarn to change the yarn color or to make the yarn pigments less toxic. Many types of yarn in different materials, thickness, and strengths, can be dyed using customized mounts 210 that insert inside the vessel 200. First we program the bioreactor for temperature and agitation speed. Then, we grow the organisms in special media to make the pigments. When there are enough pigments are produced, we insert the dyeing mount 210 and submerge the yarn in it. Depending on the type of pigment, the yarn is dyed between about 12 to about 24 hours. Then the yarn is washed, sterilized, and treated in the portable bioreactor.

Example 2

Fashion is considered to be one of the most polluting industries in the world. Thus, it is desirable to create dyes that are less toxic. The inventors herein demonstrate how microorganisms may be used to grow pigments useful in dyeing different kinds of yarn. In this example, commercial white yarn was used. With the portable bioreactor 500, microbial pigments were prepared from two different organisms. Different "snips" of white yarn were cut and placed into special mounts 210. Using these mounts 210, the white yarn is fully immersed inside liquid containing the pigments. The bioreactor is used to fasten the pigments to the yarn. To do this, a mordant was prepared (depending on the type of pigment and yarn). The mordant is a solution made of metal complexes and salts. The white yarn was first exposed to the mordant under high temperature, so as to become more receptive to the pigment. Then the yarn was soaked inside the microbial-derived pigment to accept the pigment. This provides for the ability to make a "recipe" for a desired color that can be customized at will. Previously unknown colors can be grown on demand.

We claim:

1. A portable bioreactor system for growing microbes, the system comprising:
   a portable bioreactor having a base, the base comprising a battery module configured to supply power to the portable bioreactor without access to power from an electric power grid;
   a culture vessel comprising a syringe;
   a mount disposed within the culture vessel, the mount comprising a surface for biofilm growth;
   memory;
   one or more processors; and
   one or more modules stored in memory and configured for execution by the one or more processors, the modules comprising instructions for:
   (a) agitating the culture vessel;
   (b) measuring a property of the culture vessel contents by operating a peripheral; and,
   (c) providing data to an external computer by means of a wireless connection.

2. The portable bioreactor system of claim 1, the system further comprising a spectroscope at about 600 nm of a fluid inside the culture vessel.

3. The portable bioreactor system of claim 1, the system further comprising a network communication module operably connected to the one or more processors.

4. The portable bioreactor system of claim 1, the system further comprising a web connectivity module, enabling real-time analysis of the operation of the bioreactor system.

5. The portable bioreactor system of claim 1, the system further comprising a module operably connected to the one or more processors capable of reading and writing data from wireless identification tags, including a near field communication (NFC) tag.

6. The portable bioreactor system of claim 1, wherein the system further comprises a voice control module allowing spoken commands to control the system.

7. The portable bioreactor system of claim 3, wherein the system further comprises a camera.

* * * * *